(12) United States Patent
Ertl

(10) Patent No.: US 8,662,890 B2
(45) Date of Patent: Mar. 4, 2014

(54) METHOD FOR MANUFACTURING A DENTAL RESTORATION

(75) Inventor: Thomas Ertl, Dreieich (DE)

(73) Assignee: Degudent GmbH, Hanau (DE)

( * ) Notice: Subject to any disclaimer, the term of this patent is extended or adjusted under 35 U.S.C. 154(b) by 1288 days.

(21) Appl. No.: 11/937,842

(22) Filed: Nov. 9, 2007

(65) Prior Publication Data

US 2008/0124677 A1  May 29, 2008

(30) Foreign Application Priority Data

Nov. 28, 2006 (EP) ..................................... 06024575

(51) Int. Cl.
*A61C 19/04* (2006.01)
*A61C 5/00* (2006.01)

(52) U.S. Cl.
USPC ............................................ 433/72; 433/215

(58) Field of Classification Search
USPC .............. 433/72, 75, 213, 215; 600/589–590; 700/95–98; 382/154, 128; 703/1
See application file for complete search history.

(56) References Cited

U.S. PATENT DOCUMENTS

| 6,287,121 | B1 * | 9/2001 | Guiot et al. ................... 433/218 |
| 6,925,198 | B2 * | 8/2005 | Scharlack et al. ............ 382/128 |
| 7,065,243 | B2 | 6/2006 | Boland et al. |
| 2003/0219148 | A1 | 11/2003 | Scharlack et al. |
| 2004/0015327 | A1 * | 1/2004 | Sachdeva et al. ............. 702/167 |
| 2004/0167391 | A1 * | 8/2004 | Solar et al. ..................... 600/411 |
| 2006/0281046 | A1 * | 12/2006 | Heo ................................ 433/75 |

FOREIGN PATENT DOCUMENTS

| DE | 19749107 | 5/1998 |
| EP | 1710536 | 10/2006 |
| WO | 2005058183 | 6/2005 |

* cited by examiner

*Primary Examiner* — Heidi M Eide
(74) *Attorney, Agent, or Firm* — Ladas & Parry LLP

(57) ABSTRACT

A method for manufacturing a dental restoration for at least one section of a dental arch on the basis of digital overall data which are calculated in relation to individual data, which are based on three-dimensional optical individual measurements that are performed intra-orally of an area that contains at least one section of the dental arch. In order to ensure that the overall data, which have been received from individual measurements, represent the measured section of the dental arch and/or the dental arch in its entirety without any distortions, it is proposed that at least one area of the dental arch be measured together with a reference, which supplies three-dimensional information, and calculated from the individual data while considering the reference of the overall data.

13 Claims, 3 Drawing Sheets

METHOD FOR MANUFACTURING A DENTAL RESTORATION

BACKGROUND OF THE INVENTION

The invention pertains to a method for manufacturing a dental restoration for at least one section of a dental arch on the basis of digital overall data, which is calculated in relation to individual data, that is based on three-dimensional optical individual measurements performed on an intra-oral basis of an area containing at least one section of the dental arch, whereby at least one area of the dental arch is measured together with a reference which supplies three-dimensional information, and the overall data are calculated from the individual data while considering the reference.

In order to produce dentures, it is known to produce a duplicate from one area of the dental arch where a dental restoration is to be introduced. Single scans are then produced from sections of the duplicate, which are then spatially positioned with respect to one another, in order to calculate the digital data. The respective data are then used in coordination with configurations of the restoration, which have been recorded in a library, in a CAD/CAM process to perform the restoration by means of processing, such as grinding of a blank preferably comprised of ceramic.

In order to minimize errors when calculating the data that are necessary for the manufacturing of the dental restoration, which are related to measurements, it is known from WO-A-2005/058183 how to physically assign the measured individual duplicate sections based on a reference.

DE-B-10 2004 051 165 also uses a scannable model as the basis for manufacturing the dentures, whereby scanned segments of the model are spatially positioned with respect to one another by means of a reference.

US-A-2003/0219148 provides a method for the generation of a three-dimensional model of a dental arch on the basis of digital data which are determined in relation to given individual data, which in turn have been produced by three-dimensional optical individual measurements. In order to be able to combine overlapping individual measurements by means of stitching, three-dimensional references are also scanned, which can cover areas that are to be partially scanned.

The object of EP-A-1 710 536 is a method for the three-dimensional shape capture particularly of a dental model. Areas of the model are optically measured together with a reference model, whereby corrective values are determined from the deviation between the actual and real values of the reference object.

In a method for determining the shape of a duplicate of a remaining dental area according to WO-A-2005/058183 that is to be provided with a dental restoration, duplicate sections are referenced in a spatial relationship to one another based on a reference, which is recorded in a computer.

A standard scale for use with a photogrammetric measuring device has been described in DE-A-197 49 107.

U.S. Pat. No. 7,065,243 reveals a method for producing a dental model. It determines an intra-oral measuring of one or several teeth with a concurrent presence of a reference for the position of a camera, which measures the tooth or teeth. With the camera position being a known fact in respect to the tooth or teeth, a 3-D-model is thus produced, which is then necessary to produce the denture. A corresponding method is burdensome and also shows the disadvantage that the reference, which is shaped as a square open box, shades the tooth or teeth.

The intra-oral measurement of at least one section of the dental arch is performed from different angles while the distance to the camera varies. The individual images are then combined through stitching and merging to develop three-dimensional data of the dental arch section, in order to be able to produce the desired denture based on the digitally available data. It is in this case possible that accumulations of small deviations may cause distortions of the 3-D-data set which exceed the acceptable tolerance levels.

SUMMARY OF THE INVENTION

It is the purpose of the invention at hand to develop a method of the initial type in such a manner that the overall data developed from the individual measurements reflect the measured section of the dental arch or arches without distortion.

According to the present invention, this purpose is mainly addressed by means of the following procedural steps:

a) Completion of initial, intra-oral, three-dimensional, optical measurements of at least one section of the dental arch without a reference to determine the individual data, b) Positioning of the reference (36, 38) in relation to the area, c) Completion of subsequent, intra-oral, three-dimensional, optical measurements of the dental arch area or an additional (second) area which encompasses the area of the dental arch, to determine additional individual data and d) Combining the initial individual data together with the additional individual data and with consideration of the reference to calculate the overall data resulting from the difference between measured and real geometry of the reference and with consideration given to corrective data, or e) Application of an at least partially transparent plate element with markings that extend on at least two planes as reference, measurement of at least one section of the dental arch together with the reference and calculation of the overall data.

According to the present invention it is intended to initially perform the first three-dimensional optical measurements of at least one section of the dental arch without the presence of the reference to determine initial individual data, subsequently position the reference in relation to the area, and finally perform additional three-dimensional measurements to determine additional individual data of a second area of the dental arch, which encompasses at least the initial area as well as the reference. The initial individual data is then combined with the additional individual data including the reference, in order to calculate the overall data, whereby corrective data that is the result of the difference between measured and real geometry of the reference will be considered. The measuring sequence can also be performed in reverse order, that means the dental arch and/or an area of the dental arch is measured with and then without the reference. The present invention also includes the alternative, where the dental arch and/or the relevant area of the dental arch are measured together with the reference without the performance of further measurements. The reference of the dental arch and/or the area of the dental arch may, however, in this case not shade the area where the dental restoration is to be performed.

"A section of a dental arch" shall refer to a tooth, a group of teeth or even the entire dental arch, which can be with full dentition, with partial dentition or edentulous.

According to the present invention, the reference of familiar three-dimensional geometry is either optically measured with the relevant area of the dental arch or, in the case of a partial shading, the relevant area of the dental arch is determined without the reference, in order to develop three-dimensional data of the relevant area of the dental arch by stitching and merging the individual measurements under consideration of the reference, which is used as a basis to produce the dentures. The individual measurements, which present the reference, are combined, whereby a correction of the combined measurements is performed based on the known geometry of the reference.

The individual measurements are combined in a known manner by common calculations, while taking into account the overlapping areas to create a 3-D-illustration of the dental arch and/or the relevant area to finally perform a correction of the actual reference in relation to the known reference and to develop a distortion-free 3-D-illustration, from which the necessary digital data are applied in order to produce the dentures.

When measurements are performed with and without reference, the individual measurements are, on the one hand, combined without the reference and, on the other hand, the individual measurements are combined with the reference in order to produce a three-dimensional image, and the three-dimensional images that were created are corrected by evaluating the differences between the image of the reference and their known actual geometry, that means the measured reference, i.e. the actual reference is corrected in the known actual or real geometry of the reference. A three-dimensional data set is thereby developed without showing any distortions with respect to the measured area of the dental arch. In other words, the deviations of the measured data of the reference object are used to calculate corrective data of the actual geometry of the reference object. These corrective data are applied to the distorted measurement data to correct the measurement error.

An object that has a plate-like geometry can be used as reference, whereby the object is comprised of three-dimensional protrusions and/or indentations such as pyramids or pyramid stubs, in order to enable a definite three-dimensional assignment of the individual measurement. A plate element that is at least partially transparent and has markings that continue preferably in a grid-like manner and are offset to one another and exist on at least two planes can be used, which will allow conclusions with respect to the camera position. Depending on the distance of the planes from one another and the offset of the markings in relation to each other, images are developed in relation to the position of the camera which are precisely fitted to one another based on the known position of the references, so that a distortion of the relevant area of the dental arch, which is determined from the individual measurements, is basically eliminated.

The reference should separately consist of a material with a low expansion coefficient as well as a high E-modulus, such as ceramic and/or glass ceramic, in order to minimize errors related to temperature or external forces.

BRIEF DESCRIPTION OF THE DRAWINGS

Additional specifications, advantages and characteristics of the present invention not only arise from the claims or the characteristics found therein—separately and/or in combination—but also from the preferred embodiments and the following descriptions of their illustrations.

In the drawings.

DESCRIPTION OF THE PREFERRED EMBODIMENTS

The area of a dental arch where the denture is to be inserted is measured three-dimensionally, in order to produce a dental restoration and then develop digital data from the thus developed 3-D image, which is used to produce the denture in a CAD/CAM procedure. Since the respective area and/or, if applicable, the entire dental arch cannot be captured in one image in its entirety and without shading, it is common to take several individual images, hereinafter referred to as single scans, which can then be joined together using familiar techniques such as registering, stitching and merging as can be learned, for example, from DE-A-10 2005 011 066. A disadvantage according to the state of technology becomes evident that due to a collective accumulation of small deviations, which are generated during the stitching and merging of the single scans, the 3-D data set, which is necessary for producing the dentures, contains distortions that exceed the allowable tolerance levels. In order to eliminate these distortions, the relevant area is measured according to the present invention together with a reference, which makes it possible to join the single scans in an objective and accurate manner, so that respective distortions are prevented.

Figure 1:
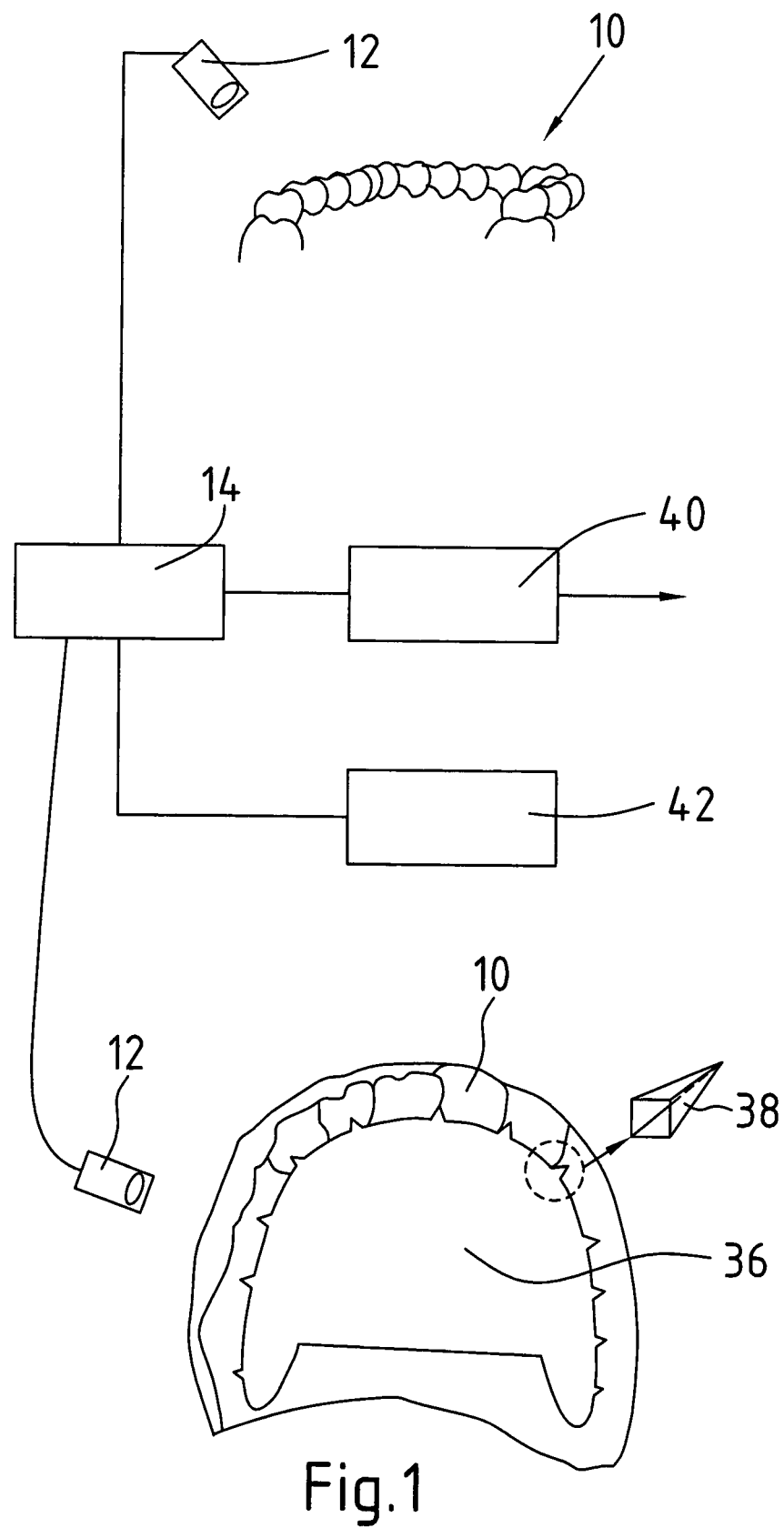
FIG. 1 is a schematic, representative illustration of the measurement of a dental area, with and without reference.

FIG. 1 shows a representative illustration of a lower jaw 10, of which a section is optically measured three-dimensionally and the single measurements are then used to establish a 3-D data set, which is necessary to produce the denture. For this purpose, a camera 12 is adjusted in various positions in relation to the lower jaw 10 to capture the relevant area from different positions. Since respective measurements are completed manually, the distance to the lower jaw 10 is thus modified, so that the individual images must be stitched and merged in order to achieve the 3-D images of the relevant areas of the lower jaw. The images captured by camera 12 for this purpose are sent to an image processor with computer 14.

Figure 2:
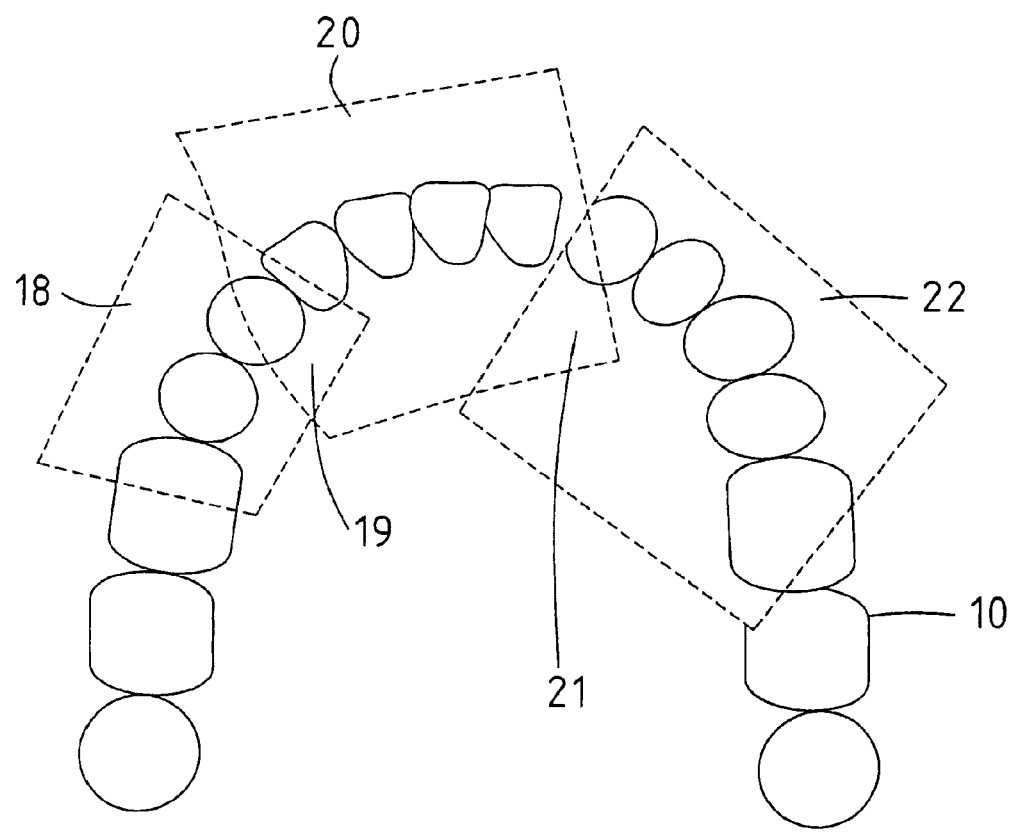
FIG. 2 is a representative illustration of a lower jaw.
Figure 3:
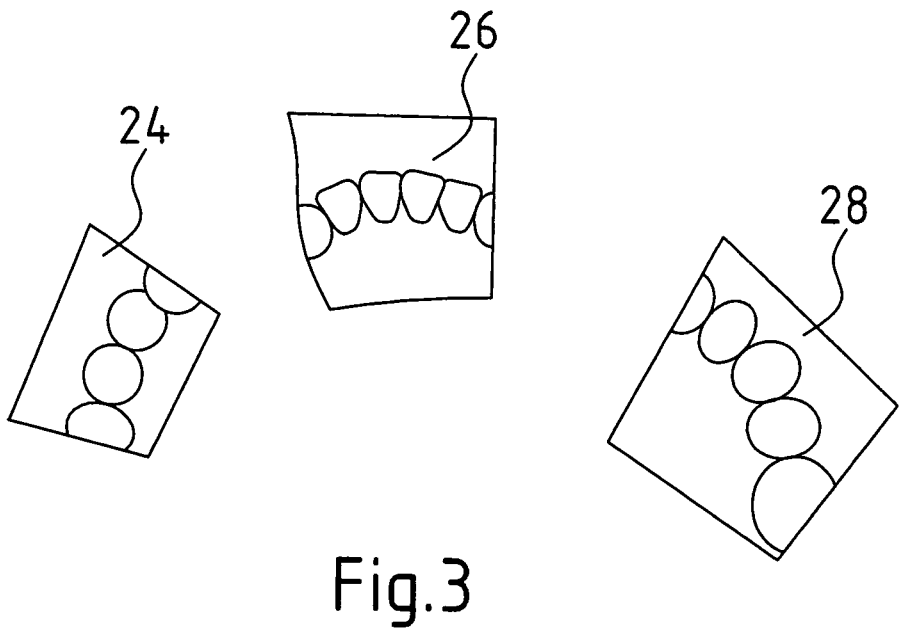
FIG. 3 shows individual images of an area of the lower jaw according to FIG. 2.
Figure 4:
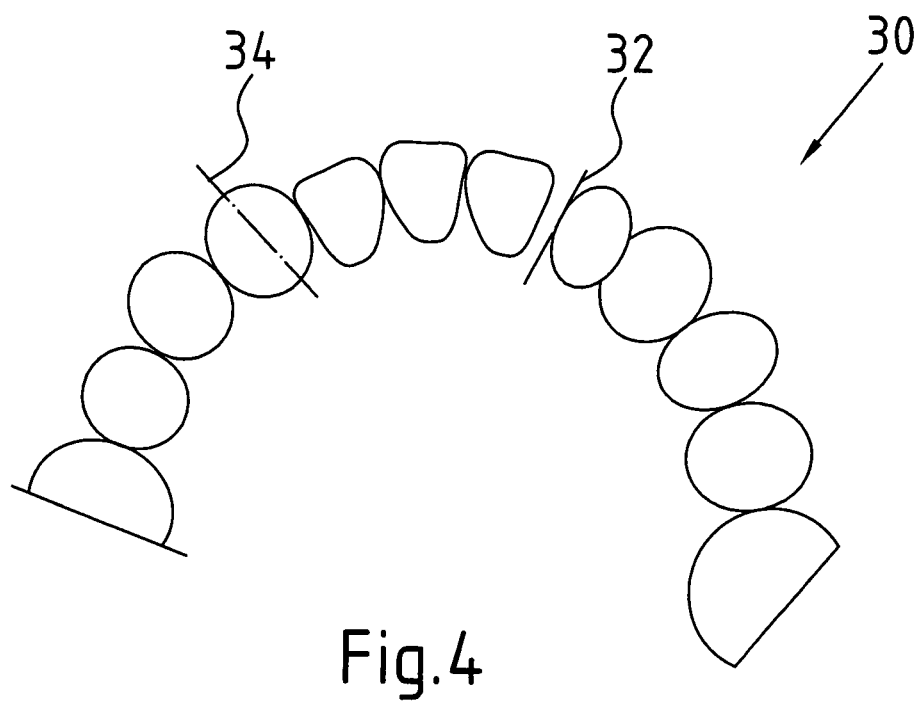
FIG. 4 is an illustration of the lower jaw according to FIG. 2 after joining of the individual images.

FIG. 2 shows the lower jaw 10 in a top view, from which in a relevant area where a dental reconstruction such as a crown or bridge is to be inserted, three-dimensional images shall be made using various angles. The images must overlap, in order to produce an overall scan or a 3-D image from the individual images (single scans) for the entire relevant area. FIG. 2 shows purely for exemplary purposes three areas 18, 20, 22 that are used to produce so-called single scans. Since the camera 12 captures the areas 18, 20, 22 at different distances and/or at angles that vary from one another, the images of the respective areas are identical neither in size nor in relation to the captured space. This shall be illustrated by means of FIG. 3. Top view images of the areas 18, 20, 22 are representative illustrations that have been taken at different distances from the lower jaw 10, resulting in different enlargements which vary from one another. The respective images are marked with the reference marks 24, 26, 28. The images 24, 26, 28 are overlapping as is shown in the overlapping areas 19, 21. Due to the overlap 19, 21, it is possible to join the individual images 24, 26, 28 to one another by means of the familiar stitching and merging. This results in a possibly necessary size adjustment, a joining of the 3-D data into a common coordinate system, a positioning with respect to one another, as well as discarding of 3-D data with a lesser degree of accuracy as long as data with a higher degree of accuracy is available within the same objective area. This can lead to a collective accumulation of deviations, as can be seen in the joined image 30 according to FIG. 4. Distortions 32, 34, which were emphasized in the illustration, are possible in the overlapping areas and can lead to errors in the three-dimensional digital data that were obtained on the basis of image 30 and thus can cause the denture to lack the precise fit necessary.

In order to eliminate these errors, the intent according to the present invention is to optically measure the relevant area of the lower jaw 10 together with a reference 36, which in turn has three-dimensional structures, in order to facilitate a definite association of the individual images while considering the position of camera 12, which results from the three-dimensional structure of the reference.

In the embodiment, the reference 36 has a plate-like shape and is placed within the dental arch that is formed by the lower jaw 10. Three-dimensional, pyramid-like protrusions 38 continue peripherally in the embodiment, which make it possible to associate the individual images. The individual images or single scans are simultaneously sent to the image processor and the computer 14 so that 3-D illustrations of the relevant area, which are determined from the measurement of the lower jaw 10 without reference, can be correlated and corrected with the images of the lower jaw 10, for which the reference 36 is applied. It is important to ensure that for the individual images of the lower jaw 10 together with the reference 36, the position of the reference 36 in relation to the lower jaw 10 does remains unchanged.

The pictures of the lower jaw 10 of the images with and without reference are harmonized with suitable software, in order to make corrections in such a manner that the reference visible on the 3-D images corresponds with the actual geometry of the reference 36.

Reference 36 in particular involves a plate-shaped element which is comprised of a material with low expansion coefficient and high E-modulus. Ceramics, such as glass ceramic, are the preferred materials.

The three-dimensional structure, which by way of example is shown in the illustration as a pyramid, originates from the peripheral area of the reference element 36 and thus makes it possible to eliminate distortions in all 6 variances.

If the embodiment is used to demonstrate that the distortion-free joining of the individual images is performed using separate pictures of the lower jaw 10 with and without reference 36, there is also the possibility to develop the necessary 3-D image of the relevant area of the lower jaw 10 from the pictures of the lower jaw, when the reference is available, as long as the reference 36 does not shade the relevant area of the lower jaw 10.

In other words, the separate images of the lower jaw 10 are performed with and without the reference, in order to eliminate any errors from the very beginning that may be caused by these shadows.

The data that has been corrected by reference 36 is then processed by the computer 14 in such a manner that digital data is sent to a processing device 40, which produces the dental restoration.

The computer 14 can first be supplied with data from a library 42, where data of dental restorations have been saved.

If the invention-related theory is demonstrated by means of a dental restoration, then there is no restriction. Moreover, the method can be applied to develop data from three-dimensional objects that have been assembled from individual images.

What is claimed is:

1. Method for manufacturing a dental restoration for at least one section of a dental arch of a mouth, based on three-dimensional optical individual measurements performed on an intra-oral basis of an area that contains at least one section of the dental arch area to obtain a plurality of individual data sets which are combined to obtain a digital overall data set, comprising the steps of:
   a) performing intra-oral, three-dimensional, optical measurements of at the least one section of the dental arch area without a reference to obtain first individual data sets;
   b) positioning a reference which supplies three-dimensional information in relation to the dental arch area;
   c) performing intra-oral, three-dimensional, optical measurements of the at least one section of the dental arch area, with the reference positioned in relation thereto, to obtain second individual data sets; and
   d) combining the first individual data sets together with the second individual data sets with consideration of the reference, to calculate thereby the overall data set including corrections resulting from the difference between measured and real geometry of the reference;
   wherein the reference is a plate-shaped element that follows the dental arch of the mouth.

2. Method according to claim 1, wherein the reference is positioned in relation to the area with no physical movement.

3. Method according to claim 1, wherein markings comprising geometric structures in the form of pyramids or pyramid stubs, protrude from or are inserted into the reference.

4. Method according to claim 3, wherein the geometric structures are comprised of ceramic or glass ceramic.

5. Method according to claim 3, wherein the geometric structures originate from a peripheral area of the reference.

6. Method according to claim 1, wherein the reference is comprised of a material with a low expansion coefficient and high E-modulus.

7. Method for manufacturing a dental restoration for at least one section of a dental arch, based on three-dimensional optical individual measurements performed on an intra-oral basis of an area that contains at least one section of the dental arch area to obtain a plurality of individual data sets which are combined to obtain a digital overall data set, comprising the steps of:
   a) positioning in relation to the at least one section of the dental arch area a reference which comprises a plate element with markings that extend on at least two planes, and which supplies three-dimensional information in relation to the area;
   b) performing intra-oral, three-dimensional, optical measurements of the dental arch area or an additional area which encompasses the area of the dental arch, with the reference positioned in relation thereto, to obtain the plurality of individual data sets; and
   c) combining the plurality of individual data sets, with consideration of the reference, to calculate thereby the overall data set including corrections resulting from the difference between measured and real geometry of the reference;
   wherein the reference is a plate-shaped element that follows the dental arch of the mouth.

8. Method according to claim 7, wherein the markings on the plate element are positioned in a grid-like manner and offset with respect to one another.

9. Method according to claim 7, wherein the reference is partially transparent.

10. Method according to claim 7, wherein the markings comprise geometric structures in the form of pyramids or pyramid stubs, protruding from or inserted into said plate element.

11. Method according to claim 10, wherein the geometric structures are comprised of ceramic or glass ceramic.

12. Method according to claim 10, wherein the geometric structures originate from a peripheral area of the reference.

13. Method according to claim 7, wherein the reference has a low expansion coefficient and high E-modulus.

\* \* \* \* \*

UNITED STATES PATENT AND TRADEMARK OFFICE
CERTIFICATE OF CORRECTION

PATENT NO.        : 8,662,890 B2  
APPLICATION NO.   : 11/937842  
DATED             : March 4, 2014  
INVENTOR(S)       : Ertl Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1428 days.

Signed and Sealed this
Sixteenth Day of June, 2015

Michelle K. Lee
*Director of the United States Patent and Trademark Office*